(12) United States Patent
Franks et al.

(10) Patent No.: US 7,384,267 B1
(45) Date of Patent: Jun. 10, 2008

(54) AUTOMATIC IDENTIFICATION OF MEDICAL STAFF TRAINING NEEDS

(75) Inventors: Dorothy B. Franks, Brentwood, TN (US); Michael C. Jones, Nashville, TN (US); John G. Jaeger, Flower Mound, TX (US)

(73) Assignee: GE Medical Technology Services, Inc., Pewaukee, WI (US)

(*) Notice: Subject to any disclaimer, the term of this patent is extended or adjusted under 35 U.S.C. 154(b) by 1769 days.

(21) Appl. No.: 09/620,520

(22) Filed: Jul. 20, 2000

(51) Int. Cl.
G09B 11/00 (2006.01)
(52) U.S. Cl. .......................... 434/219; 705/14
(58) Field of Classification Search ................ 434/350, 434/219, 323, 247, 118, 262
See application file for complete search history.

(56) References Cited

U.S. PATENT DOCUMENTS

| | | | |
|---|---|---|---|
| 4,952,928 A * | 8/1990 | Carroll et al. ............ 340/10.41 |
| 5,388,252 A * | 2/1995 | Dreste et al. ................. 714/46 |
| 6,157,808 A * | 12/2000 | Hollingsworth ............. 434/350 |
| 6,347,943 B1 * | 2/2002 | Fields et al. ................ 434/118 |
| 6,381,557 B1 * | 4/2002 | Babula et al. ............... 702/183 |
| 6,416,328 B1 * | 7/2002 | Callahan ..................... 434/322 |
| 6,496,681 B1 * | 12/2002 | Linton ........................ 434/350 |
| 6,497,655 B1 * | 12/2002 | Linberg et al. .............. 600/300 |

* cited by examiner

Primary Examiner—Kathleen Mosser
(74) Attorney, Agent, or Firm—Fletcher Yoder

(57) ABSTRACT

Data representative of operation of biomedical equipment in a medical facility is collected and stored in a centralized database. The information may be collected manually during the life of the equipment, or automatically by connection to the equipment. The data references equipment types, manufacturer, departments, locations, and other relevant information for the equipment. Based upon the collected and stored information, parameters representative of possible training needs is analyzed and reported. The parameters may include error, breakdowns, and the like. Detailed reports delivered to the medical institution may thus provide a basis for planning training to enhance performance and utilization of the equipment.

27 Claims, 20 Drawing Sheets

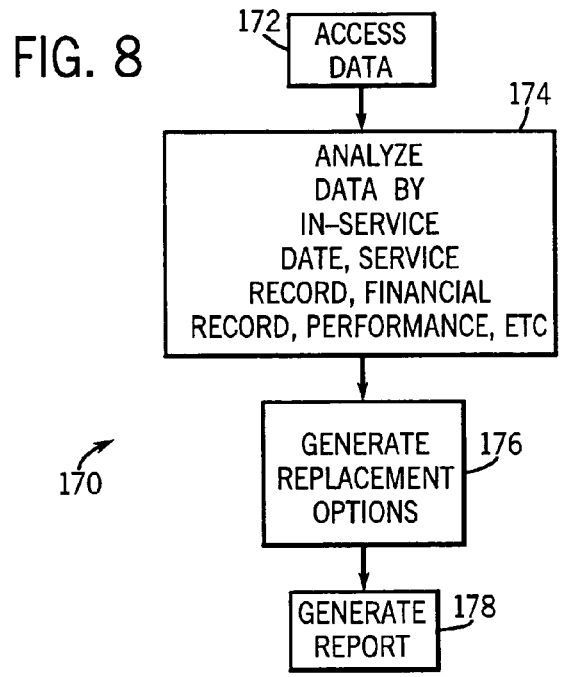
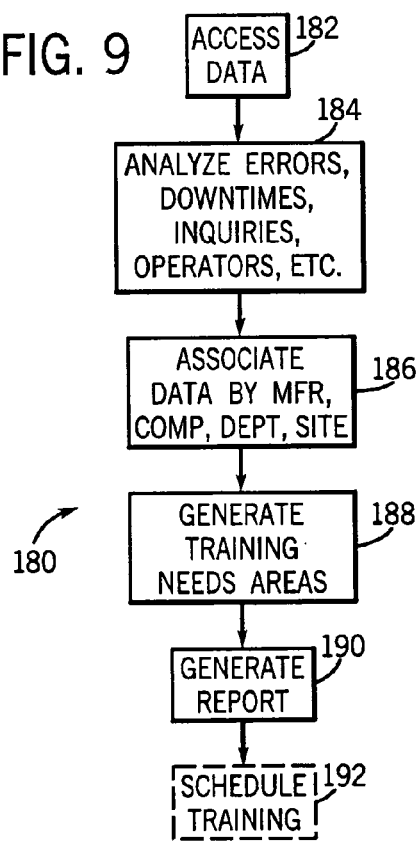
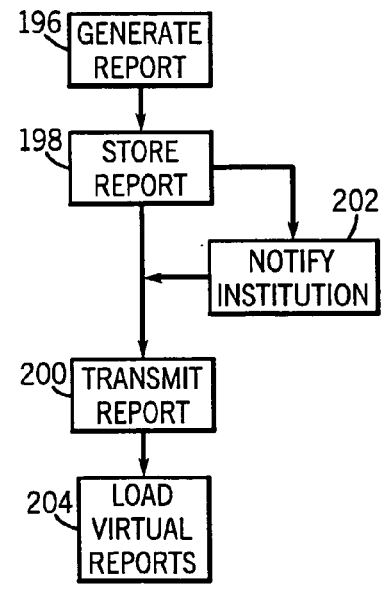

FIG. 13

FAILURE CATEGORY BENCHMARK SUMMARY TABLE (ALL FAILURES)

| FAILURE CATEGORY STATUS | STATUS | FAILURES UNDER CONTRACT | REFERENCE RANGE | REASON FOR NO STATUS |
|---|---|---|---|---|
| OTHER | ☐ | 903 | .0001 TO .0005 | |
| COMPUTER | ☐ | 144 | -.0003 TO .0004 | |
| ELECTRICAL | ☐ | 779 | .0003 TO .0011 | |
| UNKNOWN | ☐ | 9 | -.0002 TO .0002 | |
| MECHANICAL | ☐ | 1305 | .0002 TO .0009 | |
| OPERATOR | ☐ | 160 | -.0003 TO .0004 | |

☐ WITHIN REFERENCE RANGE ☐ OUTLIERS
☐ OUTSIDE REFERENCE RANGE ☐ INSUFFICIENT DATA

FIG. 17

| EQUIPMENT BY SUB-MODALITY | STATUS | ACTUAL COUNT | REFERENCE RANGE | REASON FOR NO STATUS |
|---|---|---|---|---|
| | | | EQUIPMENT COUNT BENCHMARK | |
| SUB 1 | ☐ | 34 | 6 TO 21 | REASON 1 |
| SUB 2 | ☐ | 1 | 28 TO 80 | REASON 2 |
| . | ☐ | 5 | 25 TO 131 | . |
| . | ☐ | 7 | 8 TO 23 | . |
| . | ☐ | 25 | 4 TO 22 | . |
| | ☐ | 26 | 12 TO 24 | |
| | ☐ | 8 | 2 TO 7 | |
| | ☐ | 11 | 9 TO 42 | |
| | ☐ | 265 | 114 TO 272 | |
| | ☐ | 90 | 22 TO 97 | |
| | ☐ | 57 | 13 TO 63 | |
| | ☐ | 19 | 3 TO 21 | |
| | ☐ | 148 | 63 TO 165 | |
| | ☐ | 2 | 1 TO 4 | |
| | ☐ | 383 | 230 TO 915 | |
| | ☐ | 2 | 0 TO 6 | |

270 → EQUIPMENT BY SUB-MODALITY
272 → STATUS
274 → ACTUAL COUNT
276 → REFERENCE RANGE
278 → REASON FOR NO STATUS

REPORTS CONTINUES ON NEXT PAGE
☐ WITHIN REFERENCE RANGE     ☐ OUTLIERS
☐ OUTSIDE REFERENCE RANGE    ☐ INSUFFICIENT DATA

SERVICE COVERAGE REPORT
EQUIPMENT WARRANTY BY FULL SERVICE

| DEPARTMENT | LOCATION | GROUP | EQUIP TYPE | MANUFACTURER | MANUAL | MODEL # | ACQ. DATE | CONTROL # | SERIAL # | SERVICE PROVIDER | EXP / RENEWAL DATE |
|---|---|---|---|---|---|---|---|---|---|---|---|
| DEPT 1 | LOCATION 1 | | TYPE 1 | | | # | 3/1/98 | # | # | | |
| DEPT 2 | LOCATION 2 | | TYPE 2 | | | # | 6/1/99 | # | # | | |
| . | . | | . | | | . | N/A | . | . | | |
| . | . | | . | | | . | N/A | . | . | | |
| | | | | | | | N/A | | | | |
| | | | | | | | N/A | | | | |

FIG. 21

| MANUFACTURER | EQUIPMENT | # OF BKDWNS | BKDWNS PER YR. | CONTROL # | SERIAL # | AGE/TIME SERVICE | MTTR* (DAYS) | MTBF** (MONTHS) |
|---|---|---|---|---|---|---|---|---|
| | | | | | | | | |
| | | | | | | | | |
| | | | | | | | | |
| | | | | | | | | |
| | | | | | | | | |
| | | | | | | | | |

BREAKDOWN DETAILS BY DEPARTMENT * MEAN TIME TO REPAIR
DEPARTMENT 1    **MEAN TIME BETWEEN FAILURES

FIG. 22

HOSPITAL – INSTITUTION 1

| DEPARTMENT | BREAKDOWN COUNT |
|---|---|
| DEPT 1 | 79 |
| DEPT 2 | 140 |
| . | 24 |
| . | 3 |
| . | 131 |
|  | 59 |
|  | 1 |
|  | 24 |

REPORTS CONTINUE ON NEXT PAGE...
↑ ↑
330 332

SUGGESTED INVENTORY ENHANCEMENT SUMMARY
(5 YEAR FORECAST)
INSTITUTION 1

SUGGESTED INVENTORY REPLACEMENT SUMMARY
BASED ON INDUSTRY DATA – CONTINUED

| EQUIPMENT SUB-MODALITY | CURRENT COUNT | 2004 FORECAST NEED | POTENTIAL RETIREMENTS BETWEEN NOW AND 2004 | NET ADDITIONAL NEED |
|---|---|---|---|---|
| SUB 1 | 12 | 13 | 8 | 9 |
| SUB 2 | 1 | 1 | 1 | 1 |
| . | 10 | 11 | 7 | 8 |
| . | 4 | 4 | 4 | 4 |
| . | 2 | 2 | 2 | 2 |
|  | 1 | 1 | 1 | 1 |
|  | 12 | 13 | 9 | 10 |
|  | 12 | 13 | 9 | 10 |

REPORTS CONTINUE ON NEXT PAGE...

AUTOMATIC IDENTIFICATION OF MEDICAL STAFF TRAINING NEEDS

FIELD OF THE INVENTION

The present invention relates generally to the field of medical institutions and services. More particularly, the invention relates to a technique for automatically identifying potential service personnel training needs, and for reporting such needs for planning and evaluation purposes

BACKGROUND OF THE INVENTION

Modern medical diagnostic facilities include a wide range of equipment, systems, and techniques which evolve on a continual and sometimes rapid basis. Human resources, including physicians, technicians, clinicians, nurses, and support personnel are often challenged by the advances in the field, and by the range of improvements which, if properly utilized, can dramatically enhance the quality of care provided to patients. By way of example, imaging systems and patient monitoring equipment now offer extremely powerful tools for the detection and diagnosis of disease and physical ailments which can be addressed extremely effectively if properly identified. Ongoing improvements in equipment and procedures, however, place increasing demands on the facility personnel in terms of knowledge and experience.

Conventional techniques for identifying training needs include ongoing educational programs, and special programs implemented for new and even more experienced personnel. For example, physicians, regularly attend conferences and maintain libraries on improved procedures and techniques. Nurses and clinicians similarly receive ongoing training. Moreover, where new systems or equipment are placed in service, subsequent training sessions may be held by the institution or by the equipment manufacturer to lay the ground work for use of the equipment and new procedures. While equipment manufacturers typically provide ongoing assistance, it would be preferable, in many cases, for institutional personnel to become even more autonomous in their knowledge and utilization of equipment and procedures. Training and utilization guides and materials may not provide a completely adequate basis for particular needs, and vary greatly in their quality and utility.

There is a need, therefore, for an improved technique for identifying training needs in medical facilities. There is a particular need, at present, for a system which will allow for straightforward, preferably automated, identification of certain training needs based upon utilization of equipment and systems and upon data stored within the institutions information resources. Reports and scheduling of training can then be made by the institution, or by a contractor or service provider, to enhance the knowledge base of institution personnel, and thereby to improve the quality of patient care and reduce the institutions costs in providing such high-quality care.

SUMMARY OF THE INVENTION

The invention provides a technique for identifying training needs and reporting such needs designed to respond to the drawbacks in conventional approaches. The technique may be employed in a wide range of institutions, but is particularly well suited to integrated institutions employing various system types, procedures, and over a range of departments, sites, and so forth. Moreover, the technique may be employed with existing hospital information systems (HIS) as well as with newly-installed or upgraded information systems. The technique is particularly powerful when employed over a group of individuals, equipment, departments, sites, and facilities, allowing for training on levels varying from individual care providers to entire departments or groups of care providers.

The technique may be based upon data collected in manual or automated procedures. For example, asset utilization data reflecting problems in asset use may be collected and analyzed so as to identify particular problem areas where the use of the assets may not be fully understood or exploited. Where failure, error, or problem logs are maintained on individual assets, either manually or automatically, such logs may be accessed and analyzed to determine whether procedures are being carried out effectively and efficiently, or conversely, where additional training and support may be in order. Where the data is accessed and evaluated on a more comprehensive basis, such as by department, site, or some other logical grouping, training needs may be determined by similar groupings, allowing for scheduling in a more efficient and comprehensive manner.

BRIEF DESCRIPTION OF THE DRAWINGS

FIG. 8 is a flow chart illustrating exemplary control logic for equipment replacement and planning processing;

FIG. 9 is a flow chart illustrating exemplary control logic for analysis of data to determine possible areas for staff training;

FIG. 10 is a flow chart illustrating exemplary control logic for report delivery based upon analysis summarizing the foregoing figures;

FIGS. 12-25 are exemplary report screens illustrating report analysis for biomedical equipment presenting data for departments, groups, sites, and individual equipment components and types in accordance with aspects of the present technique.

DETAILED DESCRIPTION OF THE INVENTION

Figure 1:
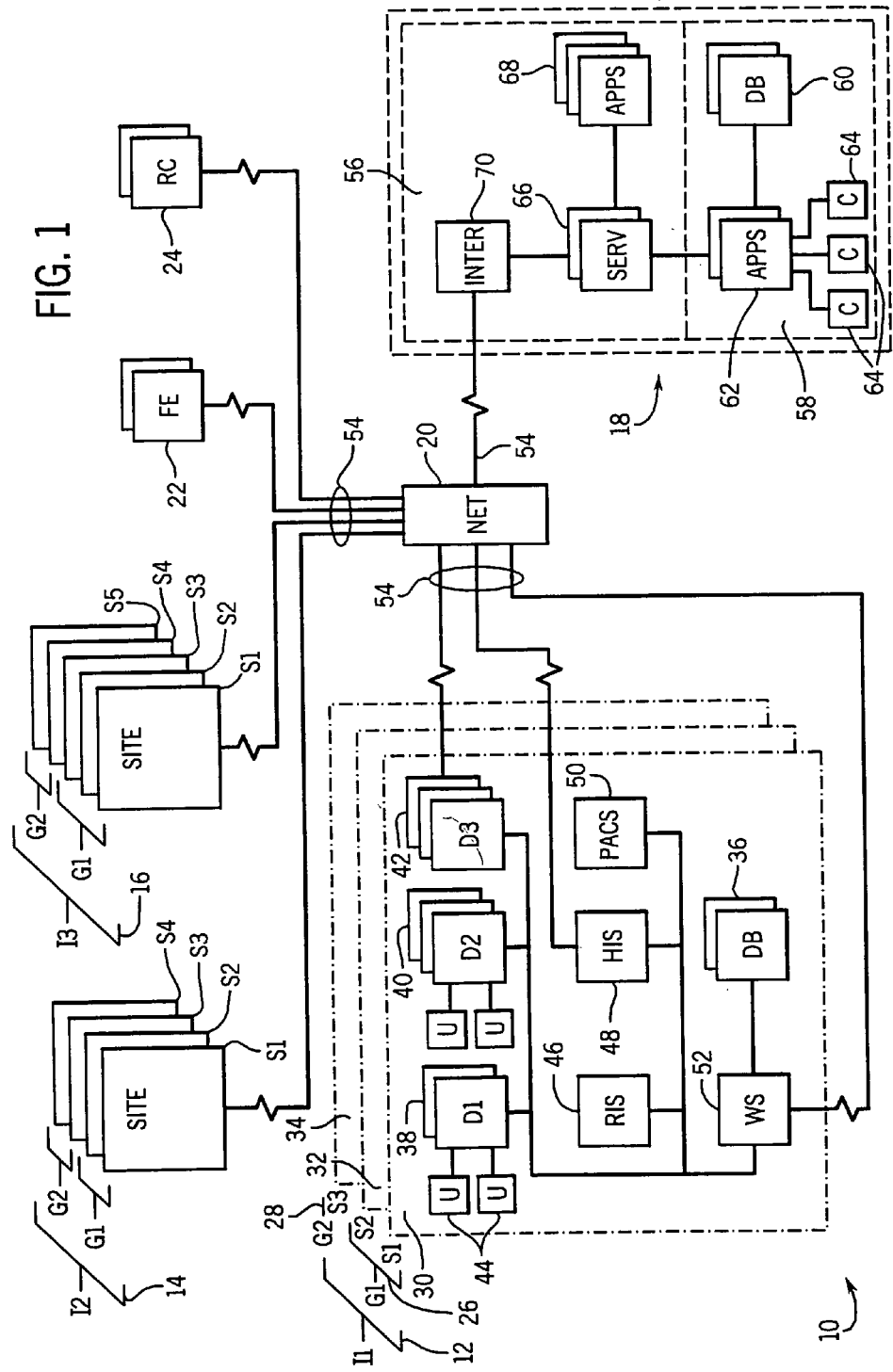
FIG. 1 is a diagrammatical representation of a service system for collecting and analyzing data in one or more medical institutions.

Turning up to the drawings, and referring first to FIG. 1, a service system 10 is represented for monitoring, data collection, data analysis, and reporting relating to biomedical equipment in one or more medical institutions. As illustrated, system 10 includes a plurality of institutions 12, 14 and 16, details of which are represented only for the first institution 12. In accordance with aspects of the present technique, any number of institutions may be serviced by a topography such as that illustrated in FIG. 1, or various modified topographies employing the techniques described below. System 10 further includes at least one service provider 18 which services the biomedical equipment of the institutions, collects and analyzes data on the equipment, and provides reports relating to the equipment inventory, performance, and so forth. In the illustrated embodiment, the institutions and the service provider may be linked via a network 20, such as the Internet. In a general implementation, the system may also permit access of data records by field engineers or technicians 22, and by remote clients 24. The field engineers and remote clients may, where appropriate, access or input data via mobile computer systems, remote computer terminals, and so forth.

Within each institution, a variety of functional portions or subdivisions may be defined, and data collected and analyzed in accordance with such functional portions. In the embodiment of FIG. 1, for example, institution 12 includes two functional groups 26 and 28, and three facility sites 30, 32 and 34. Sites 30 and 32 comprise group 26, while site 34 forms group 28. As will be described below, the present technique facilitates a collection and centralized storage of biomedical equipment data for individual sites, individual departments within the sites, institutions, and logical groupings. By way of example, where an institution includes sites in geographically dispersed locations, each site may be accounted for separately, but with the equipment data being referenced by site and institution, permitting an overview by either the site or the institution. Similarly, logical groupings, such as by political subdivisions (e.g., state, country, city) or fiscal or taxing jurisdictions may be specified and the data accordingly referenced.

Within each site, a variety of departments and systems may be designated and interfaced with one another. A centralized database 36 is compiled including data relating to biomedical equipment maintained (e.g., owned, managed, leased) by the institution. It should be noted that the database could be stored on any suitable memory device, and multiple memory devices, as shown, may be provided for storage of all or part of the database, or to provide backup and redundancy in storage. In general, however, the centralized database forms, for the user, a central repository for biomedical equipment data which can be accessed, processed, transferred, stored, and maintained to facilitate the tracking, management, planning, and other decision-making.

In the embodiment of FIG. 1, institution 12, at site 30, includes a variety of departments 38, 40 and 42. Depending upon the mission of the institution, these departments may include radiology departments, emergency care facilities, neonatal care facilities, oncology units, and so forth. Within each department, biomedical equipment will be maintained for providing medical care to in-patients and out-patients. In the present context, the biomedical equipment may include a wide range of disposable and non-disposable resources, such as patient monitors, input and readout devices, and so on. Generally, however, the biomedical equipment may also include elements of the physical plant of the institution, including beds, wheelchairs, computer systems, and so forth. In certain departments the equipment may further include imaging stations, scanners, probes, coil assemblies, and so forth. The equipment of each department is available for operation by nurses, clinicians, physicians, and other users, as indicated diagrammatically by reference numeral 44 in FIG. 1.

In addition to the biomedical equipment assigned to each department, the institution may include additional systems which are interfaced in the institution information system. For example, a radiology department information system (RIS) 46, a hospital information system (HIS) 48, a picture archiving and communication system (PACS) 50, and a similar information management systems may be provided. One or more management stations 52, such as a conventional computer workstation, is provided, preferably at each site, for reviewing reports and data generated as described below. It should be noted that a variety of such management stations may be provided, including fully or partially enabled management stations within each department. Various departments and systems within the institution will be provided with configurable network interfaces, such as modems or other network connections, so as to facilitate transmission and reception of data via network links 54 and network 20.

Service provider 18, which may function partially within the institution itself, includes processing capabilities for accessing, analyzing and reporting on data collected by the institutions on the biomedical equipment. It should be noted, however, that in the embodiment illustrated in FIG. 1, the service provider 18 may maintain facilities remote from one or more of the institutions and one or more of the facility sites, with data being transmitted between the institutions and the service providers via network 20. In the embodiment illustrated in FIG. 1, service provider 18 includes processing capabilities divided into a first processing space 56 and a second processing space 58. As described below, to maintain heightened security for data stored by the service provider, processing space 58 may be separated from space 56 to substantially limit access to processing space 58 from users outside the service provider system. In the present context, space 58 serves to store biomedical equipment records, to process data from the records, and exports data files for generation of reports within processing space 56. Thus, one or more databases 60 are maintained by the service provider 18, with processing capabilities in a form of specific applications 62 provided for storing, associating, analyzing, and extracting data from the database. Clients 64 may access the applications for performing the data manipulation functions at the service provider. One or more servers 66 are linked to the applications 62 to receive data files used as the basis for generating equipment reports. Additional applications 68 serve to format and process the reports. Finally, a network interface 70 is provided, such as including a router, modems, or similar network interface circuitry, for receiving data and transmitting data and reports to the medical institutions from the service provider.

Figure 2:
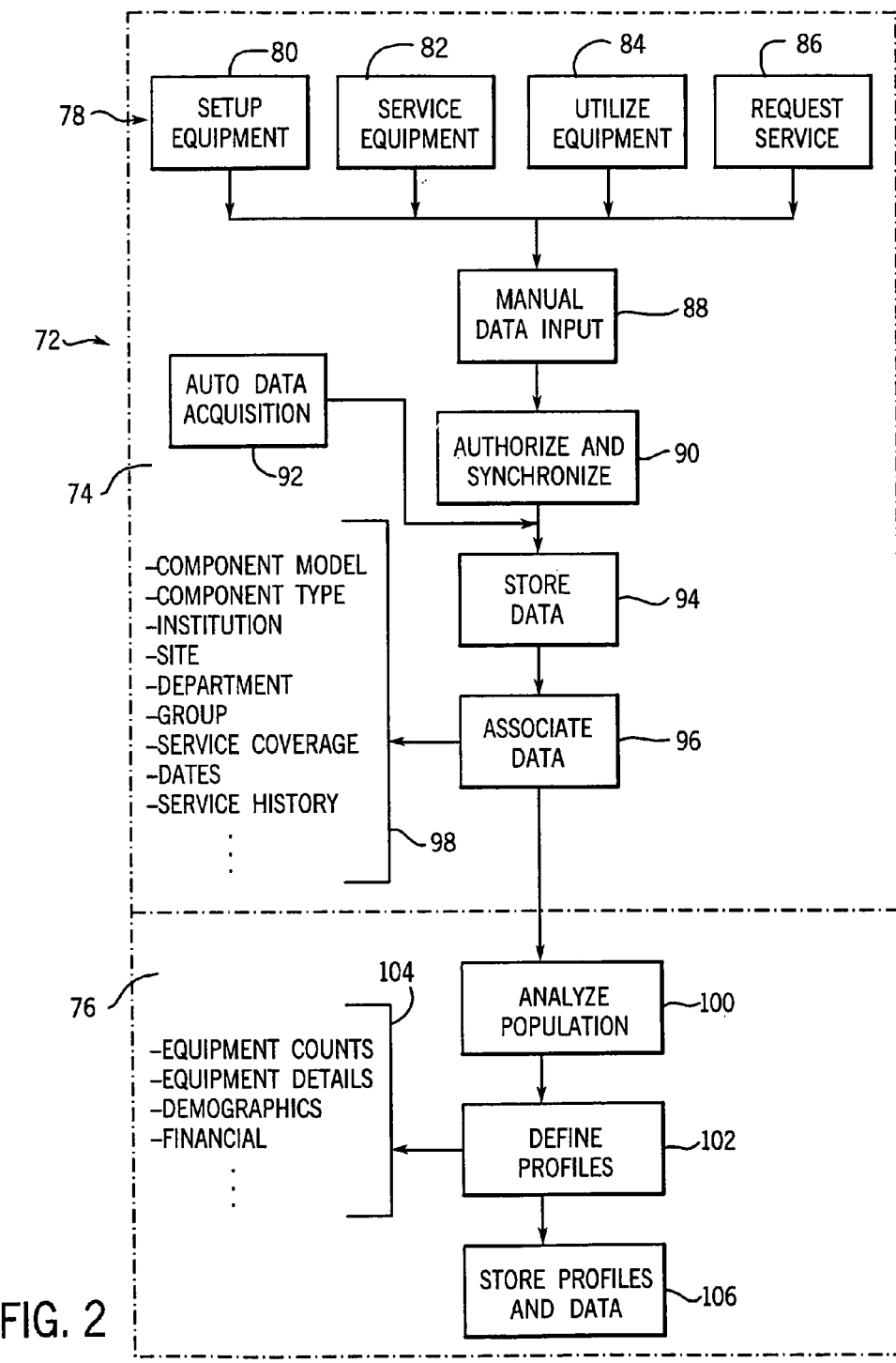
FIG. 2 is a flow chart representing exemplary control logic for collecting and analyzing the data system of the type illustrated in FIG. 1.

FIG. 2 represents exemplary logic for accessing or collecting, storing, and analyzing biomedical equipment data in a system of the type illustrated in FIG. 1. The processing illustrated in FIG. 2 may be logically subdivided into a data collection/storage/association sequence 74, and a population data analysis sequence 76. Within the sequence 74, data is collected for biomedical equipment within departments, sites, groups and institutions either manually, as indicated at reference numeral 78, or by automatic acquisition. Any suitable data input technique may be employed, typically including manual input via a workstation, laptop computer, handheld device, and so forth. Thus, as illustrated in FIG. 2, input may be by equipment setup upon its initialization, as indicated at reference numeral 80, or by subsequent servicing (i.e., as individual equipment components are serviced) as indicated at reference numeral 82. Other data may be manually input as the equipment components are utilized as indicated at 84, or upon specific service requests as indicated at reference numeral 86. At any one of these or other points in the operation of the biomedical equipment, the data relating to the equipment is thus manually input as indicated at reference numeral 88. To limit access to the data input system, and to maintain the integrity of the data, an authorization and synchronization sequence 90 is preferably implemented, such as through password protection, permitting authorized personnel only or authorized stations to input equipment data. Synchronization is performed to maintain up-to-date equipment data once the input is performed.

As an alternative to manual data input, certain automatic data acquisition may be performed as indicated at reference numeral 92 in FIG. 2. Automatic data acquisition may include polling of certain equipment, such as at regular intervals or according to a regular schedule. Networked equipment may thus be tracked and its performance monitored through data stored at the equipment and transmitted at step 92. Following either step 90 or 92, the data is stored as indicated at reference numeral 94. As noted above, the data may be stored at one or more storage devices, but with the data being associated in a centralized database for the institution. Again, the centralized database may be located physically at one or more of the institution sites, or off-site, such as at a location of the service provider 18.

At step 96, the data collected for the biomedical equipment is associated in the centralized database in accordance with any number of logical references. The data itself preferably includes references which facilitate or comprise the association as indicated at reference numeral 98. Thus, the component data may include both the identification of the component, the component model, including its manufacturer and model designation, and a component type, typically indicated by the function of the equipment. The data also preferably includes a reference representative of the institution, the site at which the components are located, the departments to which the components are assigned, if assigned, and the group designation for associating the departments or sites logically. The service data for each component also preferably includes a reference to service agreements or contracts for all or partial coverage of the components, including original warranty data and after-purchase service contracts or subscriptions. Relevant dates are preferably included, such as the date of purchase or entry into service, dates of servicing, and expiration or renewal dates for service arrangement coverage. Moreover, specific service history information may be included, where individual components have been regularly serviced or serviced on an as-needed basis. Such service history data may also include error codes, service request records input by the institution or users, breakdown records, downtime records, subcomponent replacement records, and so forth.

The population data analysis sequence 76 permits benchmarking or profiling of specific institutions and groups of institutions in accordance with equipment usage characteristics and other considerations. Where the service provider has access to equipment records for a range of institutions, the records are preferably analyzed to identify commonalties between the institutions, sites, departments, and groups. Such analysis may include consideration of the types of institutions, the types of departments, the types of equipment utilized, and the utilization characteristics (e.g., number of components, duty imposed on components, replacement or service records, and so forth). Based upon the analysis, characteristic profiles are identified which correspond to typical institutions, sites, departments, or groups that may be used as a basis for comparing a particular institution by equipment inventory and utilization for benchmarking purposes. It should be noted that benchmarking analysis preferably results in profiles which do not identify any individual institution, but which identify only a larger groups of institutions (such as groups of 20 or more) considered representative of a particular profile. The profiles, defined at step 102, may thus include reference data 104 such as equipment counts, equipment details, demographics, and financial profiles. At step 106 the profiles and corresponding reference data are stored, preferably in the database for the service provider, for future reference in benchmarking and service planning as described below.

Figure 3:
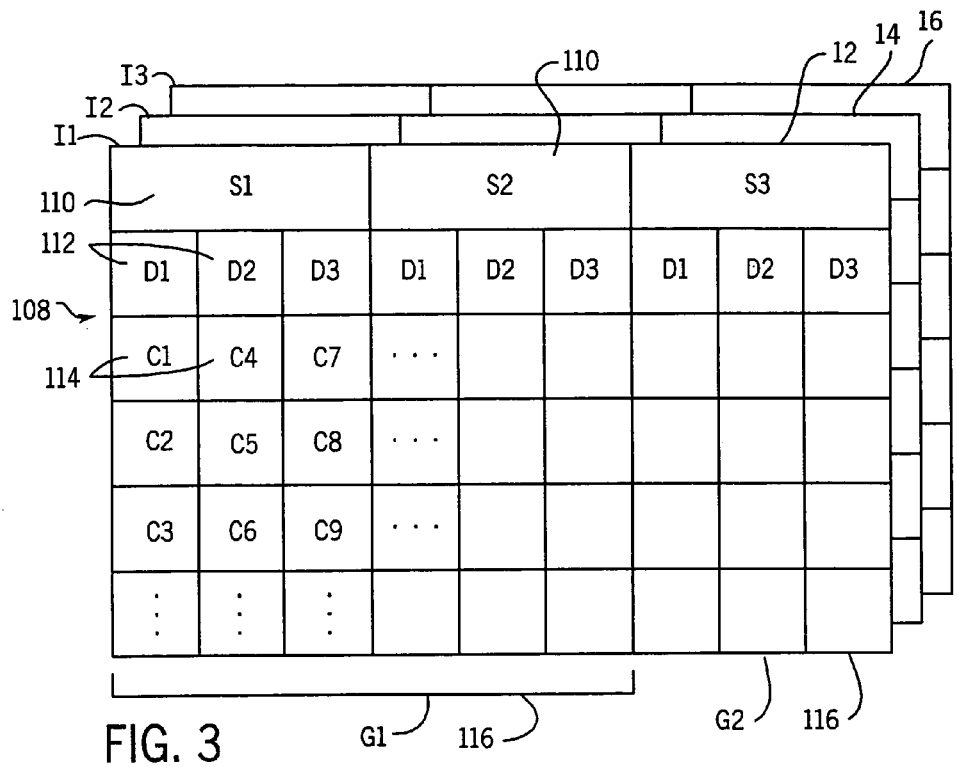
FIG. 3 is a diagrammatical representation of data records including data associated with institutions, sites, departments, groups, and components collected and processed in accordance with the aspects of present techniques.

The biomedical equipment records stored in the centralized database thus form a dataset or structure which permits and facilitates analysis by institution, site, department, group, component, component type, and other reference features. The database records may be considered to form a multidimensional data matrix structure which inter-relates these various aspects of the equipment component data as illustrated in FIG. 3. As shown in FIG. 3, the data record 108 for an institution 12 may thus include references 110 to specific facility sites at which equipment components are located. Additional departmental records 112 specify the department to which equipment components are assigned. Records for each department and site are then maintained for each component at reference numeral 114, including the identification and service information of the type described above. Moreover, the site, department, and component records may be associated by group designations 116. Where additional institutional records are available to the service provider, these may form a similar databases as illustrated in FIG. 3, permitting the analysis of groups of institutions to establish the profiles mentioned above.

Figure 4:
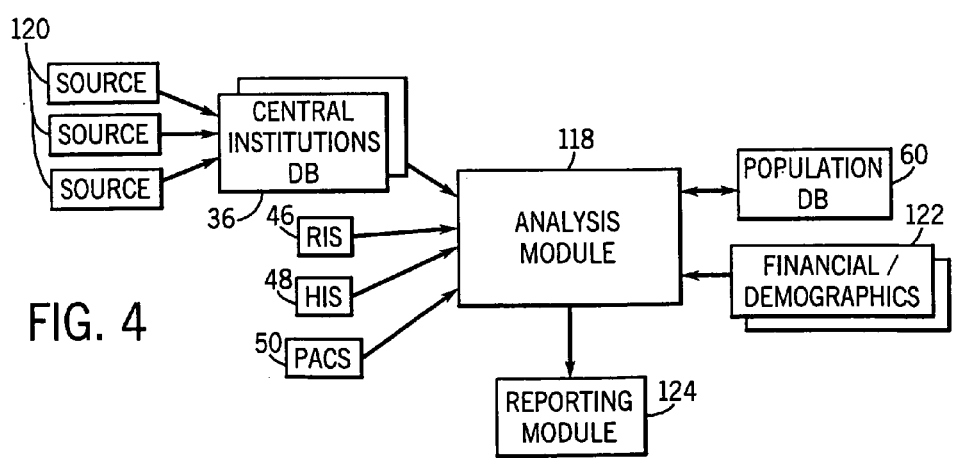
FIG. 4 is a data flow diagram illustrating the multiple sources of data utilized in analysis and reporting of institutional biomedical equipment data.

It should be noted that the present technique provides not only a centralized database for maintaining medical institution equipment records, but integrates a wide range of informational sources both at the institution and sources available to a service provider. FIG. 4 illustrates diagrammatically an example of the types of information sources which are integrated through the present technique. As described below, an analysis module 118 is provided either at the institution, or preferably at the service provider for accessing and analyzing the equipment records. The analysis module may incorporate a range of analysis algorithms, search techniques, and software applications, for deriving useful management data from the component records. In a general sense, the analysis module performs counts, statistical analysis, and associations of the equipment components by site, department, institution, group and manufacturer, as well as by any other references provided in the component records. The analysis module draws such information from the institutional database 36, as well as from other information systems of the institution, such as the RIS 46, the FHS 48, any PACS 50 present in the institution, or other institutional information systems. Again, the central institution database 36 may, in turn, obtain information from various sources, designated generally by reference numeral 120 in FIG. 4, such as departmental data entry systems, stationary or mobile data input devices, field engineer or service personnel laptops, and so forth. Similarly, analysis module 118 accesses information from population databases 60, such as for comparison in benchmarking, as well as financial, demographics, and other input 122, which may include publicly available sources, such as searchable databases, industry-specific databases, and so forth. Based upon analysis performed by the analysis module 118, a reporting module 124 is provided for generating and delivering reports representative the component records, and analysis derived from the component records.

Figure 5:
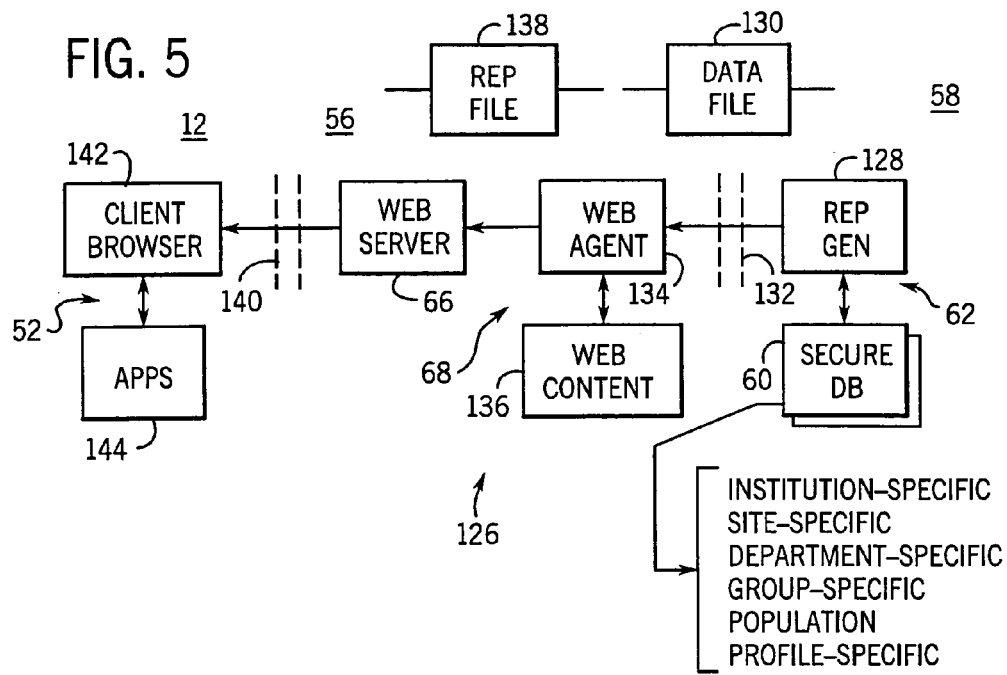
FIG. 5 is a work flow diagram illustrating functional components for securely generating reports based upon collected equipment data and for delivering the reports to a medical institution.

FIG. 5 is a diagrammatical representation of reporting workflow, designated generally by reference numeral 126, for operation of the analysis and reporting modules of FIG. 4. As shown in FIG. 5, the service provider secure database 60 is maintained in the secure processing space 58. Among the software applications 62 operative in the secure processing space 58, is a report generation application 128, which forms part of the reporting module represented generally at reference numeral 124 in FIG. 4. On a periodic basis, or upon request, the report generation application 128 accesses the data record 108 (see, e.g. FIG. 3) for the institution, and calculates or derives any inter-related data not already contained in the record for use in a management report or reports to be transmitted to the medical institution. In the example illustrated in FIG. 5, the data record includes information which institution-specific, site-specific, department-specific and group-specific. Moreover, database 60 may also include a data representative of known populations of medical institutions, sites, groups, or components, as well as pre-calculated data which is profile-specific. As noted above, the profiles generated based upon known population data may categorize institutions and other logical groupings by size, demographics, and so forth. Report generation application 128 produces a data file 130 containing data or fields of data, which is then exported via a firewall 132 to processing space 56.

Within processing space 56 additional hardware and software components are provided for translating the data file 130 into one or more report files. Thus, in the illustrated embodiment, applications 68 within the processing space 56 include a web agent 134 which is adapted to place data from file 130 into a predefined report template. Other web content, and input for generating the report is provided in one or more files 136. By integrating the data file and web content in the predefined report template, a report file 138 is generated, which may be adapted for presentation in any suitable manner, such as an HTML page on a conventional web browser. The report file 138 is then stored and is available for distribution via a web server 66.

In a present implementation, the web server 66 transmits the report file 138 via a configurable network link, such as the Internet, and through a firewall 140. At the medical institution 12, and typically at a management station 52, a client browser application 142 facilitates viewing and navigating through various portions of the report as described more fully below. Additional applications 144 may be available for manipulation of the report, formatting of the report, printing of hard copies and so forth.

Figure 6:
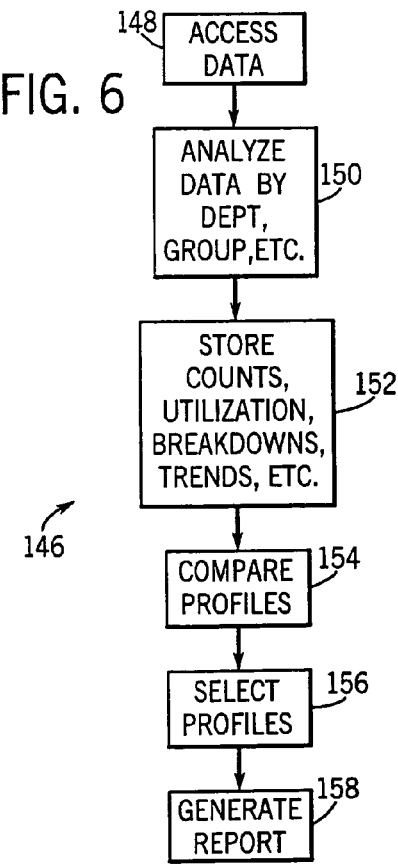
FIG. 6 is a flow chart illustrating exemplary control logic in departmental and group data processing in accordance with aspects of the present techniques.

As noted above, the present technique permits analysis of biomedical equipment data by various functional portions of a medical institution, such as by department or group. The data stored in the centralized database and accessed by the service provider is thus referenced by the functional portions, typically a department to which equipment components are assigned, or a site and group in which the components are located. FIG. 6 illustrates exemplary steps in control logic for processing the data to generate reports of equipment by department, group, site, or other logical division.

As shown in FIG. 6, at step 148, the data is accessed from the centralized database, and at step 150 the data is analyzed by the desired logical subdivision, such as the department or group. In a presently preferred embodiment, data is analyzed to identify the number of each component model and type, as well as to determine utilization parameters (e.g., time utilized or operations performed), breakdowns, error codes, trends, and so forth. Moreover, current data may be analyzed along with historical data stored in the centralized database, or in a historical database, to identify trends in these parameters over time. Thus, the analysis performed at step 150 may identify increases or decreases in the numbers of equipment components, increases or decreases in errors, breakdowns, and so forth. At step 152, the data generated by the analysis of step 150 is stored for later use in generating a report to the medical institution as described above. At step 154, all or some of the data originally collected, or derived from the original data, may be compared to reference data for similar institutions in accordance with predefined profiles as described above. The data itself may serve as the basis for selecting a comparable profile after the comparison of step 154, as indicated at step 156. Based upon the selected profile, benchmarking parameters may be generated which may provide an overview of the equipment inventory, performance, utilization, and servicing of the biomedical equipment of the institution with comparable institutions as defined by the profile. At step 158 a report is generated in accordance with the department, site, and group designation as described above with respect to FIG. 5.

Figure 7:
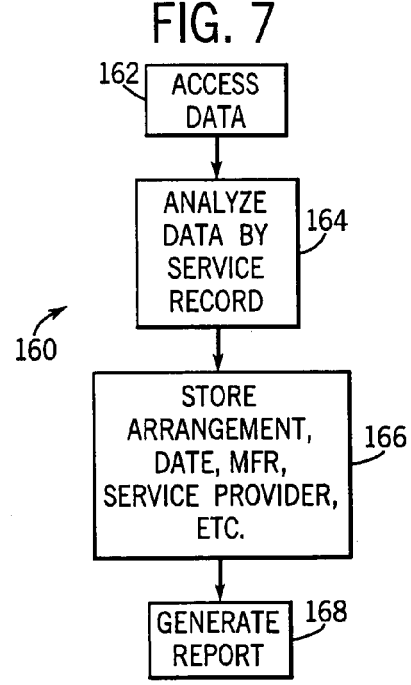
FIG. 7 is a flow chart illustrating exemplary control logic for service arrangement analysis and processing.

The present technique also permits detailed analysis of service arrangement coverage for biomedical equipment. As indicated by the control logic 160 summarized in FIG. 7, processing of the stored data to identify a service arrangement coverage begins at step 162 where the data is accessed. At step 164, the equipment records are analyzed by service record, to identify the equipment identification, its type, any existing warranties, service arrangement and subscriptions, and so forth. It should be noted that this information may include designations by department, site, group, or any other appropriate subdivision of the institution as summarized in FIG. 6. The resulting data summaries are stored at step 166 for generation of a report at step 168.

An additional functionality of the present technique permits the equipment data to be analyzed for scheduling or planning replacement of equipment, expansion in inventory, reductions in inventory, servicing, and so forth. Exemplary logic in the planning processing is summarized in FIG. 8 and designated generally by reference numeral 170. The processing 170 begins with access of the data at step 172, followed by analysis of the data by parameters such as the in-service date, the service record, financial records, performance records, and so forth. For example, specific biomedical equipment components may be scheduled for replacement a predetermined time after they are placed in service, such as in accordance with depreciation schedules, scheduled turnover of equipment, and so forth. Moreover, service records may provide a forecast of anticipated replacement needs for the equipment. Similarly, error codes or breakdown records may serve as the basis for forecasting possible replacement of the components. Where appropriate, anticipated changes in demographic information may also be used in the analysis of step 174, such as to plan for future expansions or reductions in inventory in accordance with anticipated needs of the institution. It should also be noted that, where desired, the replacement and planning processing of FIG. 8 may be performed for specific departments, sites, groups and other functional portions of the institution. At step 176, based upon the analysis of step 174, counts and types of equipment replacement are forecast and stored. Where desired, these forecasts may include accounting for anticipated costs of replacement, such as based upon current costs of the replacement items. At step 178 a planning report is generated based upon the analysis and replacement options.

A further type of processing which may be facilitated by the present technique is directed to identifying potential training needs based upon utilization of the biomedical equipment components. FIG. 9 represents steps in exemplary control logic for carrying out this processing, as indicated generally by reference numeral 180. The processing begins at step 182 where data for the components is accessed from the centralized database. At step 184, the data is analyzed to identify factors which may be indicative of a need for staff training. By way of example, such factors may include logged errors, downtimes, service or procedural inquiries, and so forth. In addition to identification of the particular components and training-indicative parameters, the data may also be analyzed to identify specific operators or users who may benefit from additional training. At step 186 the data is associated to identify the training needs by factors such as the equipment manufacturer, the component type, the department, the facility site, and so forth. Based upon the analysis made at steps 184 and 186, training needs are identified at step 188, and a report reflecting possible needs is generated at step 190. Again, the report generated at step 190, which may be generated in accordance with FIG. 5, may indicate specific training needs for specific equipment or equipment types, and may identify specific departments, sites, groups, or even specific users which may benefit from the training. As an optional step, actual training may be scheduled as indicated at step 192.

The various analyses and report generation steps described above, carried out generally in the secure manner summarized in FIG. 5, may produce reports which can be transmitted by various means to the management decision makers of the medical institution. FIG. 10 illustrates a presently preferred manner of transmitting the reports via a configurable network. The process, designated generally by reference numeral 194, begins with generation of the report as indicated at reference numeral 196. At step 198 the report is stored, such as by generation of a data file, and combination of a data file with a report template to produce a report file or files. The report may be transmitted directly to the medical institution electronically, such as via a configurable network connection, as indicated at reference numeral 200. Alternatively, a notification may be sent to the institution, such as through the configurable network, notifying the institution that the report is available for downloading as indicated at step 202. The institution may then pull the report at any convenient time. Once the report is transmitted to the medical institution, it may be loaded and viewed on a management workstation as indicated at step 204. It should be noted, that the foregoing reports may be generated separately or in combination. Moreover, in a present embodiment, a single report file may include a wide range of "virtual reports" each of which includes details or user viewable pages with specific information relating to components, departments, sites, groups, and so forth.

The reports provided by the present technique may be formatted in any suitable manner. However, in a present embodiment, the reports are generated electronically, and are transmitted to the medical institution via a configurable network connection, such as in the form of HTML pages which can be opened and viewed in a conventional web browser or other display application. FIGS. 11-25 illustrate exemplary pages in such reports generated through logic such as that described above and based upon information collected in centralized database of a medical institution.

Figure 11:
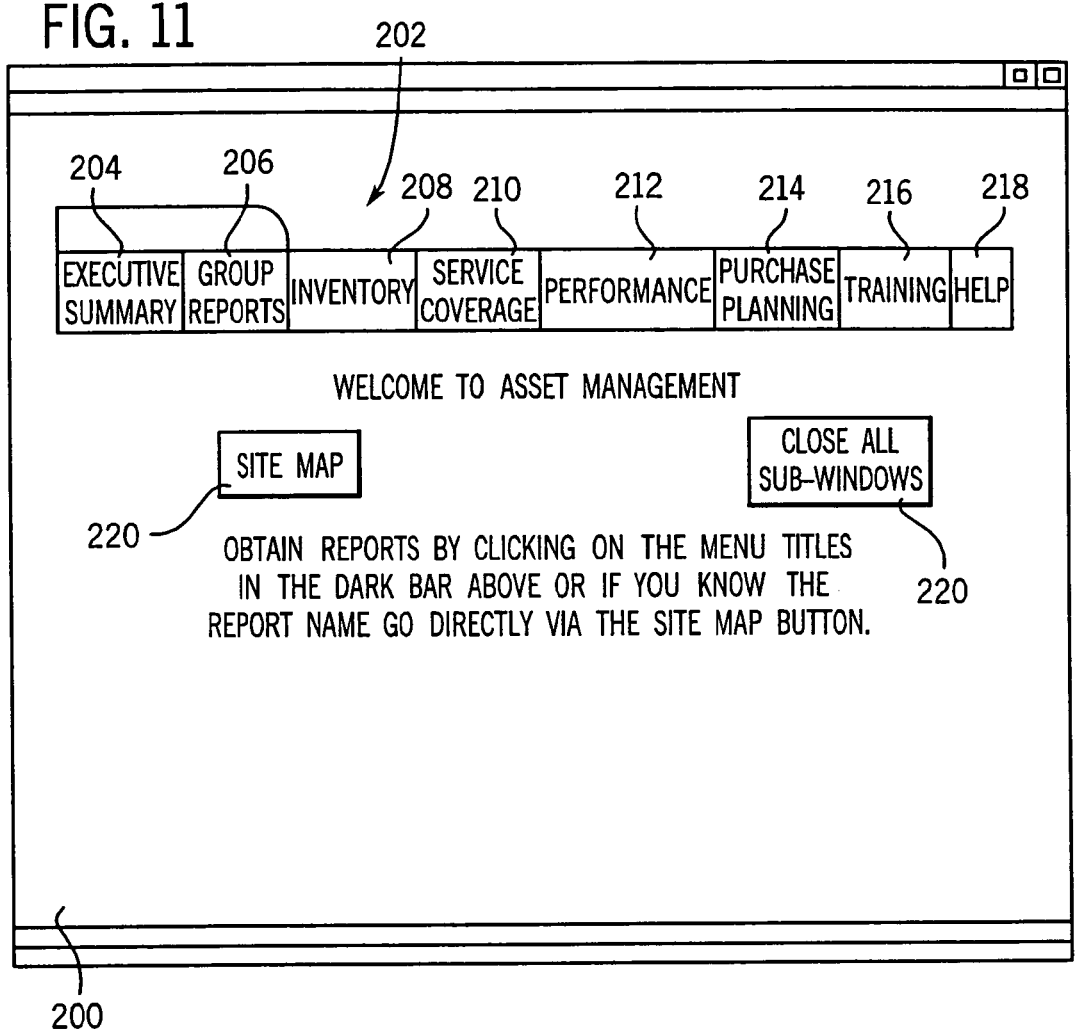
FIG. 11 is an exemplary graphical user interface screen, such as a browser screen, for accessing analyzed data and virtual reports.

FIG. 11 illustrates a summary or navigation page which is accessed in a conventional web browser for viewing additional report pages. As noted above, the report delivered in accordance with the foregoing techniques may include a wide range of data subdivided and associated in a manner so as to present information for individual equipment components, groups, sites, and so forth. In the present embodiment, the page illustrated in FIG. 11, designated generally by the reference numeral 200, provides for navigation through the various "virtual reports." The page preferably includes graphical user interface tabs or buttons 202 which can be selected by user for navigating through the more detailed reports. In the illustrated embodiment, such virtual buttons are provided for an executive summary 204, group reports 206, inventory analysis 208, service coverage analysis 210, performance analysis 212, planning analysis 214, and training analysis 216. Additional tools can be provided, such as a help tool 218, as well as alternative navigational tools 220, permitting the user to directly access virtual reports or to navigate or exit the report. As will be appreciated by those skilled in the art, various additional tools (not represented) can be provided, such as tools for reviewing previous pages, advancing to further pages, printing pages, searching through pages, and so forth.

Figure 12:
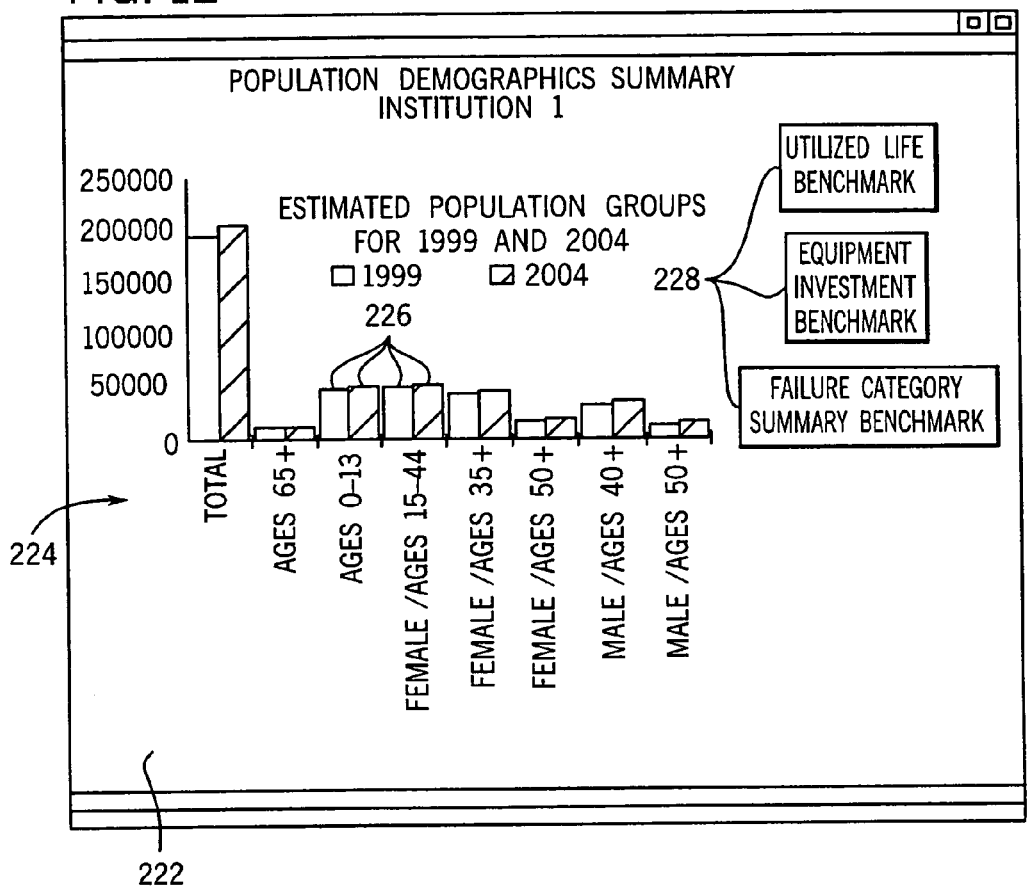

FIG. 12 illustrates an exemplary demographics summary page accessible through the executive summary tool 204 of FIG. 11. As noted above, the biomedical equipment data can be analyzed in accordance with demographic information for the institution so as to represent such factors as population groups within the institution (e.g., in-patients and out-patients), as well as the equipment utilized for patient care. In the summary page 222 of FIG. 12, a graphical summary display 224 provides an indication for the patient demographics of the subject institution. Also as noted above, where trending analysis is performed based upon current and historical collected data, trend graphics 226 may be provided. Also as noted above, where desired, equipment data collected for the institution, site, group, or department may be compared against profile data for known populations for similar institutions, and detailed benchmark reports comparing the subject institution to the selected profile may be accessed through virtual buttons 228. In the illustrated embodiment, such benchmarking is available through page 222 for comparing utilized life of equipment, investment, and failure records.

FIG. 13 illustrates a failure of benchmark summary table accessed through one of the virtual buttons 228 of FIG. 12. As illustrated in FIG. 13 the summary page 230 provides specific details for categories of equipment, as called out in a category column 232. When the collected equipment data is compared to similar data for a selected profile, the collected data may be classified in accordance with various classification ranges 234, to provide an indication of whether the subject institution's equipment performance falls within a statistical range of performance for the institution profile, or outside the range. Moreover, a summary may be provided as indicated at column 236 for equipment performance (e.g., failures) for equipment components covered by service arrangements. In the embodiment of FIG. 13, additional details are provided for the reference range in column 238 corresponding to ranges for the selected profile of the institution. Further comments and status data may be provided in additional column 240.

Figure 14:
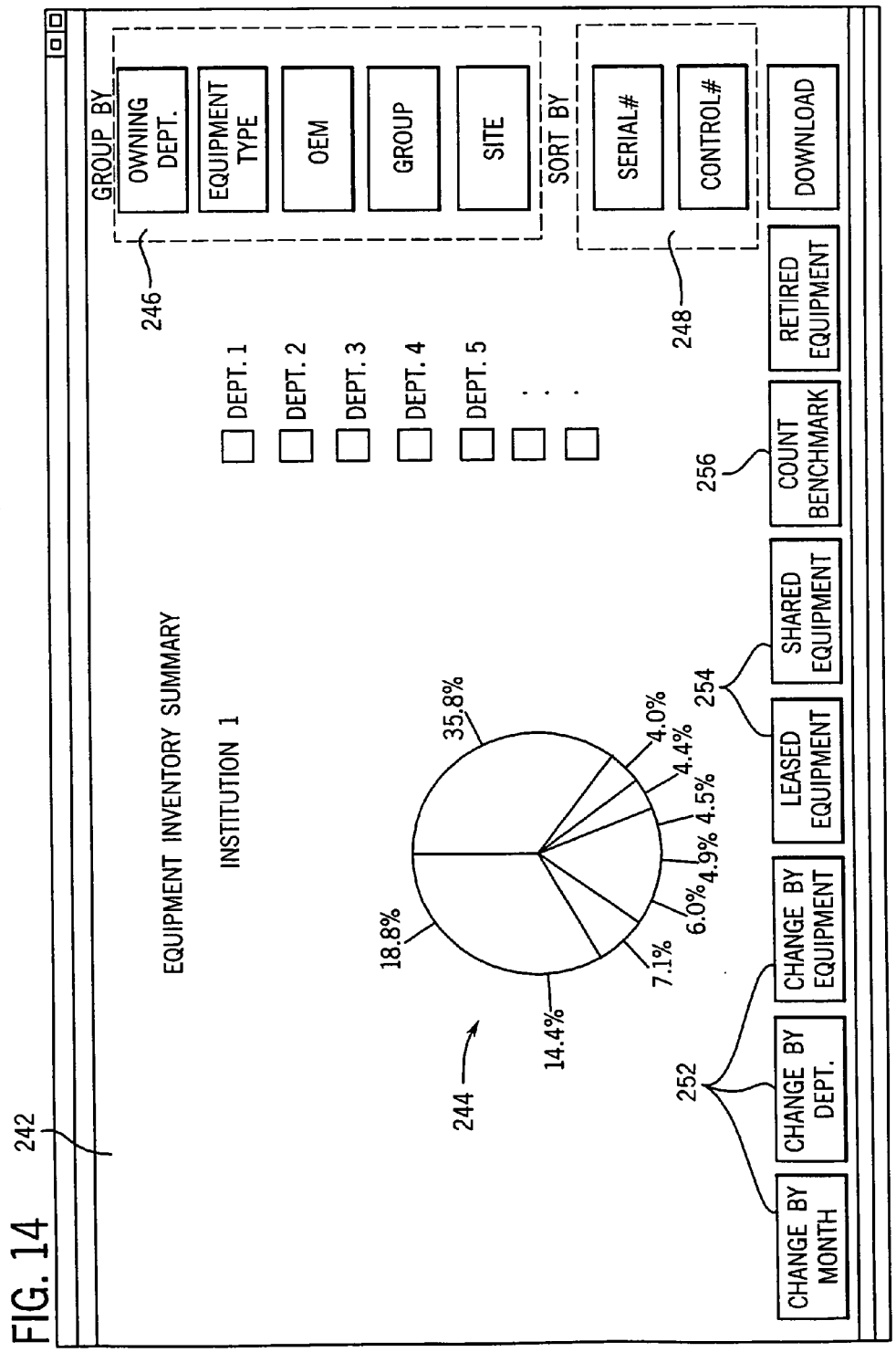

The biomedical equipment component data may also be summarized to analyze inventory on such bases as department, group, site, and so forth. FIG. 14 illustrates an inventory summary page by department as accessed through a virtual button 208 from the page illustrated in FIG. 11. As shown in FIG. 14, such inventory data may be summarized in a page 242, through the use of graphical techniques such as a graphical summary by department 244. The graphical techniques may present the data in any suitable fashion, such as through the pie chart illustrated in FIG. 14, through bar charts, line charts, or any other useful data presentation tools. In the embodiment illustrated in FIG. 14, the inventory summary page permits classification or sorting in accordance with a range of parameters stored for the equipment. By way of example, such classification may include the equipment type, the equipment manufacture, the group to which the institution or site locations belong, the site at which the equipment is located and so forth as indicated by the group tools 246. Additional sorting tools 248 may be provided, such as for viewing equipment details by serial number, control number, and so forth. As noted above, where equipment data is analyzed over a time range, such as by reference to historical equipment counts and performance, trending tools 252 may be provided, such as for viewing summary pages representing the changes by month, department, equipment, categories, and set forth. Moreover, depending upon the equipment title status, tools 254 may be provided for accessing pages presenting equipment inventory by title or ownership classifications. Finally, where benchmarking analysis is performed by reference to institution profiles and comparison to profiles for known institutions, benchmarking tools 256 may be provided for display of such comparisons.

Figure 15:
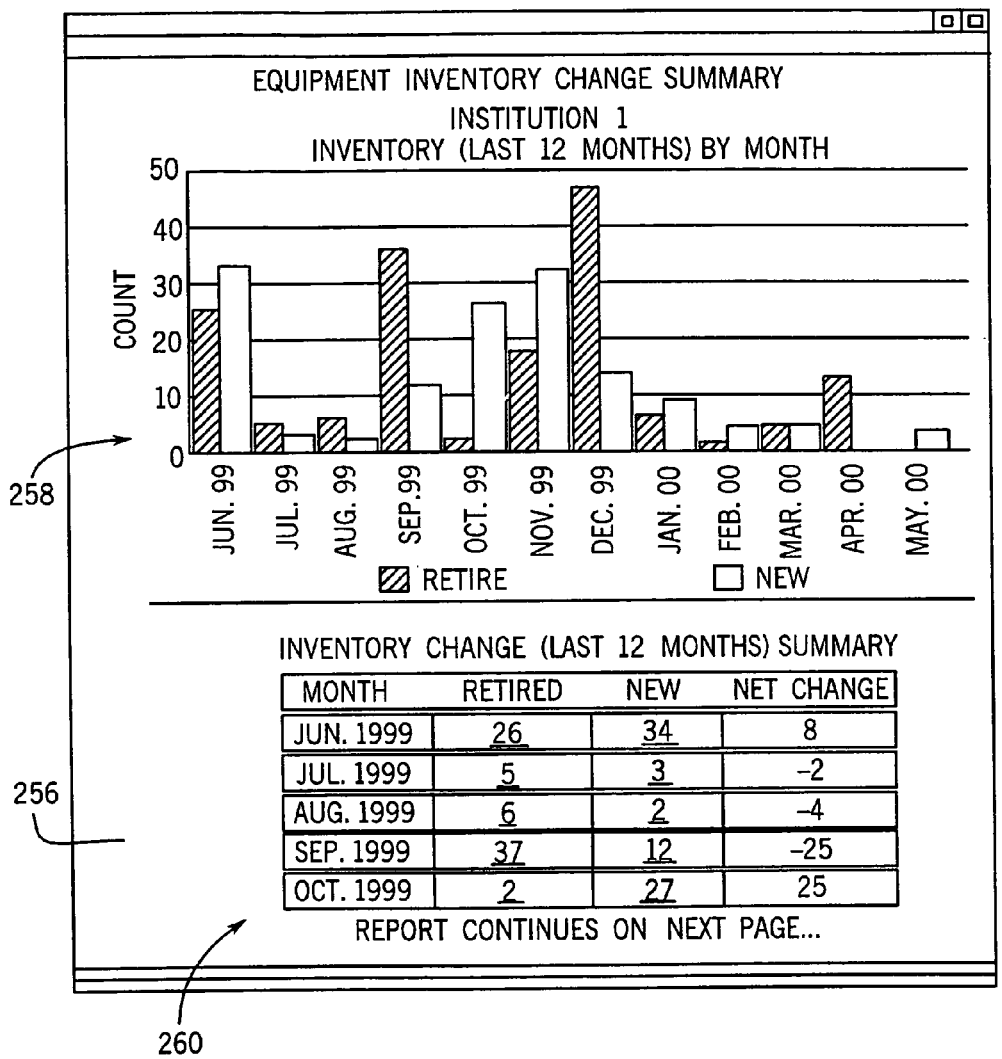
Figure 16:
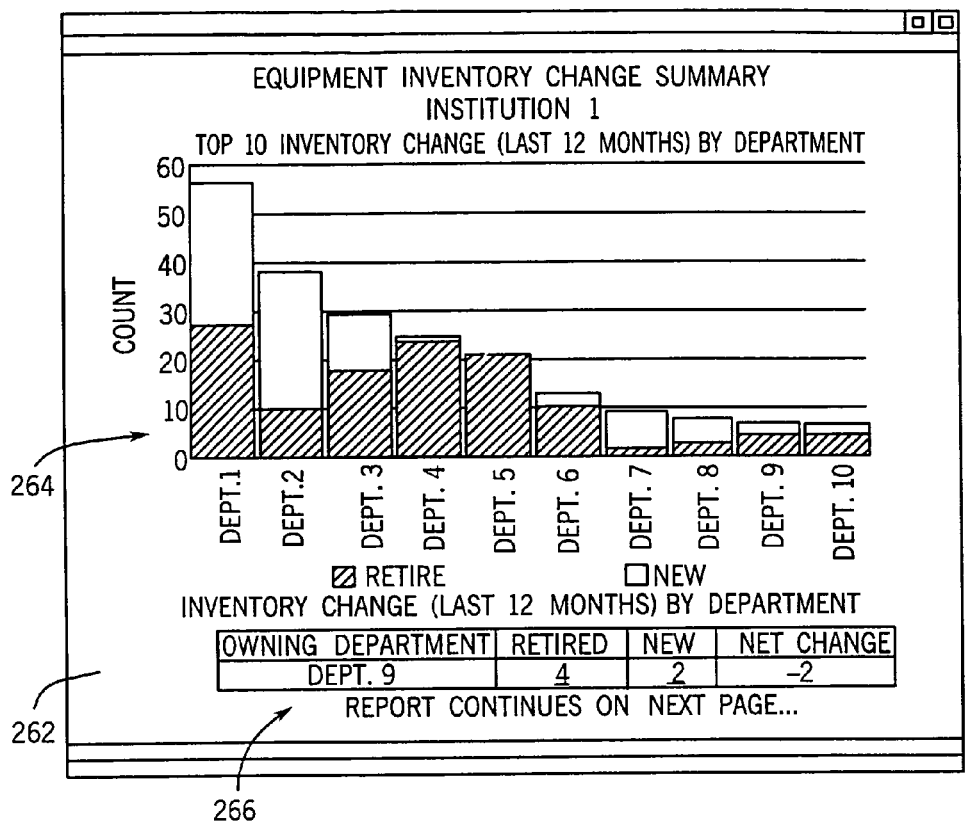

By way of example, FIG. 15 provides a page summarizing inventory trends or changes over a 12 months period, indicating both new equipment and retired equipment for an institution, as accessed via a virtual button 252 from FIG. 14. The inventory change summary page 256 provides a graphical summary 258 of the inventory changes. It should be noted that the graphical presentation may also present such changes by department, site, group, or any other desired functional portion of the institution. In the embodiment of FIG. 15, the information is also presented in a tabulated presentation indicating numerical counts for changes represented in the graphical presentation. Where desired, additional specific details may be offered through further pages, such as to provide an indication of the specific equipment or equipment types which have been retired or acquired. FIG. 16 illustrates an exemplary detailed summary page by department accessed through an additional virtual button 252 of FIG. 14. The departmental trend page 262 also provides a graphical indication 264 of the equipment changes per department, as well as a numerical count presentation 266 reflecting the changes.

As will be appreciated by those skilled in the art, the various presentations of inventory, inventory trends, inventory investment, and so forth, may be provided on various bases. For example, in the pages illustrated in FIGS. 14, 15 and 16, equipment counts are represented. However, by reference to the financial records for the institution or from a manufacturer, specific investment figures may be illustrated in a similar manner. Also, by reference to the financial records for individual components, and to regulations for taxing authorities (e.g., referenced by the group designations for the site locations) data presented in the reports may reflect book values for the equipment, depreciation to-date for the equipment, anticipated depreciation or book values, and so forth.

The comparison of the inventory data with similar data for institution profiles provides the opportunity to compare and benchmark the specific institution equipment performance. FIG. 17 illustrates an equipment count benchmark page accessed via a virtual tool 256 from the page of FIG. 14. When compared to the institution profile selected for the institution of interest, the benchmark information may compare such factors equipment counts, equipment investment, equipment performance, equipment failures, and so forth. Moreover, the information may be presented in accordance with various divisions or functional portions of the institution, such as departments, groups, sites, or as illustrated in FIG. 17 by sub-modalities. In the embodiment of FIG. 17, the benchmark presentation page 268 includes a category 270 for the equipment sub-modality, as well as a range classification column 272 indicating whether the basis for the comparison was within or outside a statistical range for the profile. An actual count column 274 is provided for each sub-modality, as well as a reference range column 276 for the specific profile selected. Other information, such as comments or status may be provided in a column 278. By way of example, in a present embodiment, where the profile population is insufficient to provide a reliable statistical basis for comparison (e.g., less than 20 institutions) a comment may be provided in column 278 indicating that this is the reason for a "no status" reference in the benchmark presentation.

Figure 18:
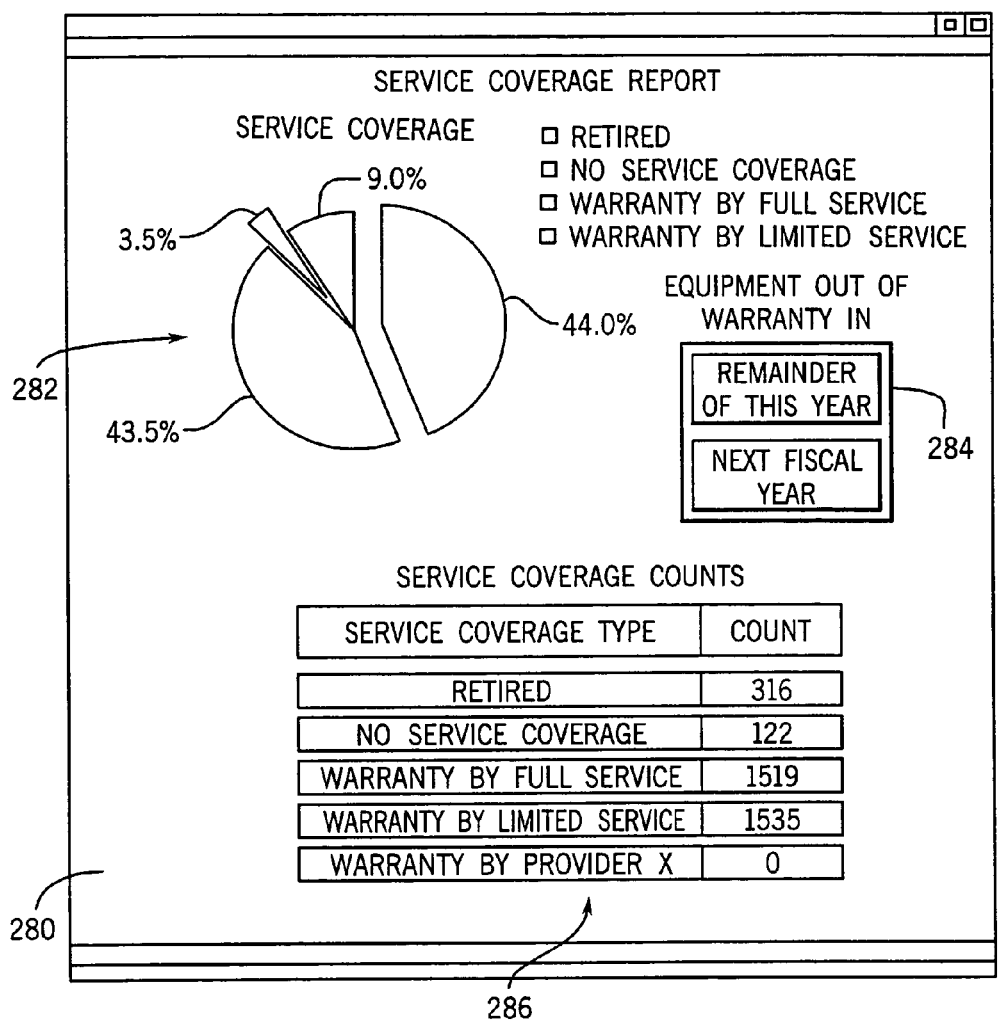

As described above, the present technique also provides an extremely useful tool for analyzing service coverage of biomedical equipment of the institution. FIG. 18 illustrates an exemplary report page summarizing service coverage for such equipment. The summary page 280 conveniently provides a graphical summary 282 for the level of service arrangement coverage or specific biomedical equipment. The page also provides tools 284 permitting the user to navigate to more detailed pages summarizing trends in service coverage, particularly service arrangements which will extend through a desired period and summaries of time periods during which service coverage will expire. Additional data presentations 286 may be provided for summarizing counts or quantities of various types of equipment which are covered by service arrangements.

FIG. 19 illustrates an exemplary detailed report of service arrangement coverage for biomedical equipment accessible from the summary page illustrated in FIG. 18. In the example FIG. 19, detailed information is provided in a summary page 288, and may be sorted in a variety of manners depending upon the analysis desired by the user. By way of example, designations or references may be provided by departments 290 to which the equipment is assigned, by site location 292 at which the equipment is located, or by group 294 to which the site belongs. The information may also be presented by equipment type 296, and equipment manufacturer 298. Where desired, more detailed reports for each of these classifications may accessible from the summary page. Additional details 298 may be provided, such as manual numbers, model numbers, and so forth. Where desired, acquisition dates for the equipment may be provided in column 300, particularly where such dates serve as the basis for warranty or other service coverage. Detailed identification numbers may be provided as indicated at reference numeral 302, specifically identifying pieces of equipment and reference codes used by the institution for designating the equipment. Moreover, where desired, specific identifications of service providers 304 and expiration and renewal dates 306 for service arrangements with the providers may be summarized. Such summaries thus provide decisions makers for the institution with powerful tools for grouping and analyzing service coverage arrangements for specific equipment, and for anticipating needed changes or renewals in such coverage.

Figure 20:
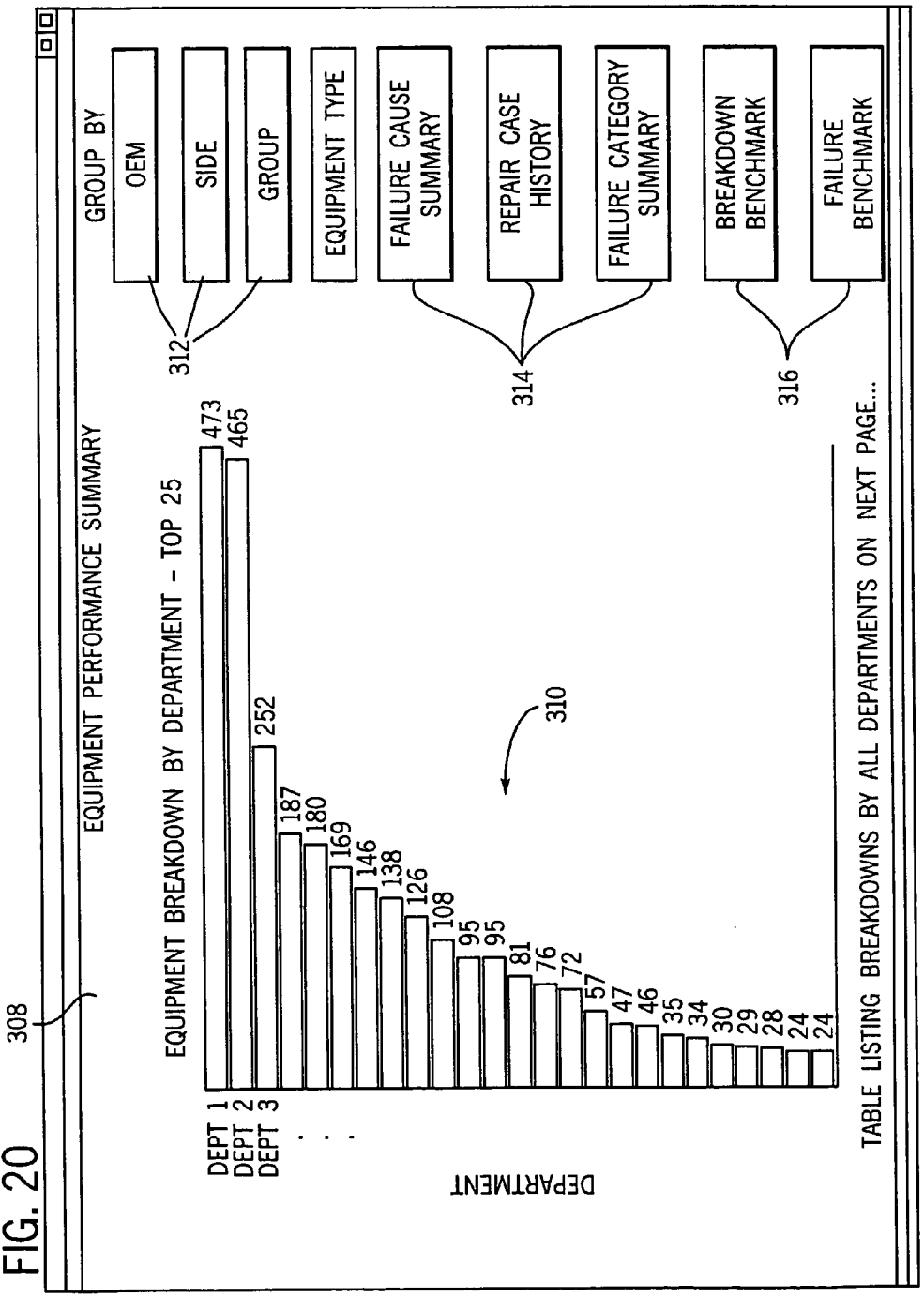

The equipment data stored in the centralized database for the institution may also be analyzed to identify parameters indicative of equipment performance. Such factors may include equipment utilization (e.g., number of days or cases for which the equipment was used) error codes, downtime, number of breakdowns, and so forth. An exemplary performance summary page 308 is illustrated in FIG. 20, accessible via a virtual button 212 from the main page of FIG. 11. In the exemplary embodiment of FIG. 20, the summary page provides a graphical summary 310 of specific equipment breakdowns by department. Similar presentations are available for other group designations, such as by equipment manufacturer, equipment site, site groups, and so forth, as indicated by the graphical buttons 312 in FIG. 20. Specific detailed analysis tools 314 may also be provided, such as for accessing virtual report pages summarizing causes of failure, repair histories, failure categories, and so forth. As noted above, the performance data may be compared against similar data for profiles of institutions derived from known populations of institutions, and benchmark pages may be presented through navigation tools 316, such as to provide breakdown benchmarking, failure benchmarking, and so forth.

By way of example, FIG. 21 illustrates a summary page for equipment performance (referenced by breakdowns) for a specific department of an institution. The departmental summary page 318, in the illustrated embodiment, provides references to the manufacturer of the equipment, as well as the equipment designation as indicated by reference numeral 320. Breakdown summary information 322 is provided, including a count of the breakdowns and a summary of the performance over a desired analysis, such as a year. Specific identifications for the equipment are provided in columns 324, allowing for tracking of individual problematic equipment components, useful in analysis, replacement, and similar planning. Finally, additional details, such as time-in-service, and statistical information such as mean-time-to-repair, and mean-time-between-failures may be summarized as indicated at reference numeral 326. Further details may be accessible through detailed pages such as illustrated in FIG. 22. The detailed page 328 of FIG. 22 may present the performance information by functional portion of the institution, such as departments as illustrated at reference numeral 330, along with detailed analysis, such as a breakdown count as indicated at reference numeral 332.

Figure 23:
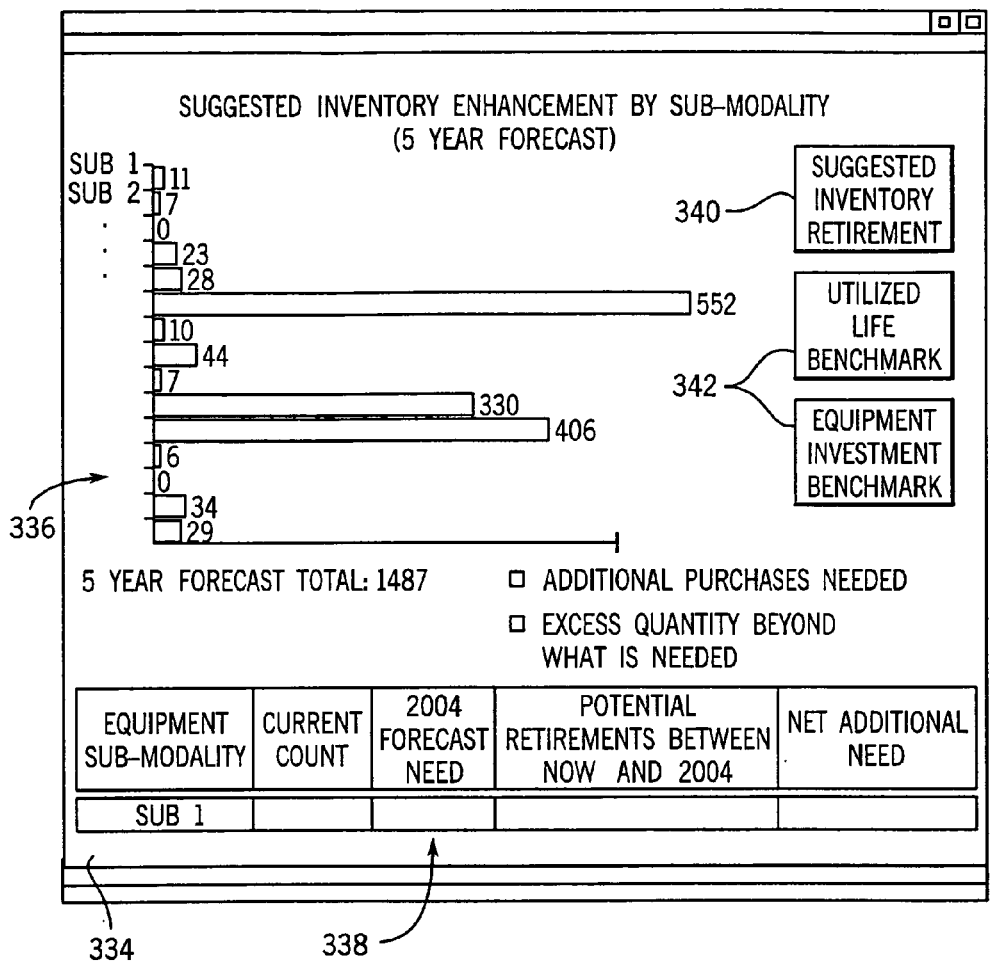

To aid in equipment management, forecasting, financial planning, and so forth, the present technique offers for data collection and reporting by analysis of potential needs for the institution, both in terms of newly acquired equipment, or retired equipment. Such forecasting tools may be based upon analysis of the equipment data stored in the centralized database, and upon factors such as the date at which the equipment entered into service, the anticipated life of the equipment, the depreciation period for the equipment, increases in anticipated demographics for the institution, and so forth. An exemplary forecast planning page 334 is illustrated in FIG. 23, accessed through a virtual button 214 from the main page at FIG. 11. As illustrated in FIG. 23, such pages may present forecasts by functional portion of the institution in graphical form 336. Such presentations may, as before, be subdivided by any suitable functional portion of the institution, such as departments, sites, groups, or as illustrated in FIG. 23, by sub-modality. The summary page may allow for additional navigation to suggested inventory changes, as indicated at reference numeral 340, as well as to benchmarking summaries for suggested equipment changes as indicated at reference numeral 342, providing comparisons of the suggested changes in the equipment inventory as compared to other institutions of similar profiles. Tabulated summaries of the data provided in the page may be summarized as indicated at reference numeral 338.

Figure 25:
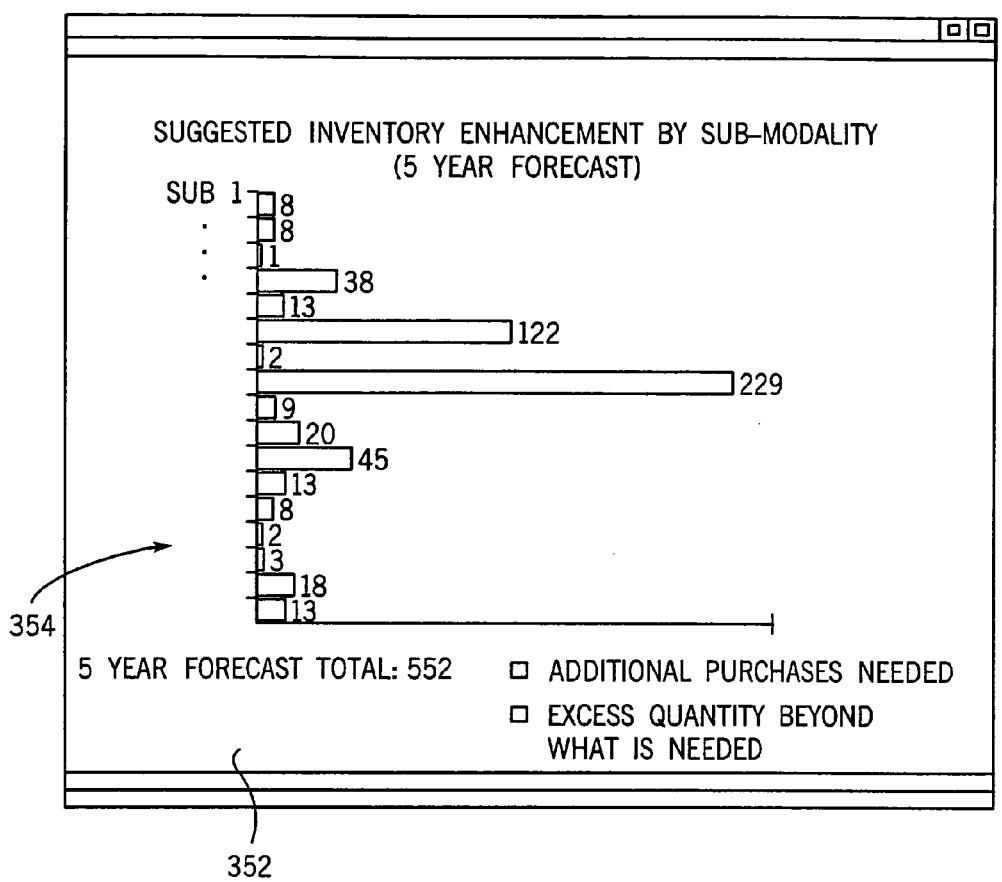

Additional, more detailed summaries accessible through the page illustrated in FIG. 23 are shown in FIGS. 24 and 25. As illustrated in these figures, a detailed planning page 344 may summarize specific changes suggested for the biomedical equipment, such as broken down by functional portion 346, in this case sub-modality. Current equipment counts (or equipment values) may be provided as indicated at reference numeral 348, as well as summaries of additions to, retirements from, and net changes in the inventory, as summarized at reference numeral 350. Even more detailed pages may be provided as shown in FIG. 25, such as through a long-term detailed forecast 352. A graphical summary 354 may be provided for the forecast, and a forecast may be subdivided by any suitable functional portion of the institution, sub-modality in the example of FIG. 25.

While the invention may be susceptible to various modifications and alternative forms, specific embodiments have been shown by way of example in the drawings and have been described in detail herein. However, it should be understood that the invention is not intended to be limited to the particular forms disclosed. Rather, the invention is to cover all modifications, equivalents, and alternatives falling within the spirit and scope of the invention as defined by the following appended claims.

The invention claimed is:

1. A method of identifying training needs for biomedical equipment in a medical institution, the method comprising:
    collecting identification and operation data associated with a plurality of biomedical equipment components;
    storing the collected data in a central database;
    analyzing the operation data to identify at least one operational parameter affected by operator activities with the equipment components;
    identifying a training need based on the analyzed operational parameter; and
    outputting a report indicating the identified training need.

2. The method of claim 1, wherein the operational parameter includes operational errors for a type of equipment component.

3. The method of claim 1, wherein the operational parameter includes failures for a type of equipment component.

4. The method of claim 1, wherein the data includes equipment type, and wherein the training need is identified by analyzing the operational parameter for a plurality of equipment components of the equipment type.

5. The method of claim 1, wherein the data includes data representative of individual operators utilizing the equipment components.

6. The method of claim 1, wherein the medical institution includes a plurality of departments, and wherein the data includes data representative of the department to which equipment components are assigned.

7. The method of claim 1, wherein the medical institution includes a plurality of geographically dispersed facility sites, and wherein the data includes data representative of the facility site at which equipment components are located.

8. The method of claim 1, wherein the report is generated at a location remote from the medical institution and is transmitted to the medical institution by a configurable network link.

9. The method of claim 8, wherein the network link includes the Internet.

10. The method of claim 1, comprising the further step of associating the stored data into groups by equipment type, and wherein the training need is identified for an equipment type group.

11. The method of claim 10, further comprising associating the stored data into groups by equipment location, wherein the training need is identified for an equipment type group and an equipment location group.

12. The method of claim 1, wherein the data further identifies an equipment manufacturer for each equipment component, and wherein the training need is identified for equipment components from a particular equipment manufacturer.

13. The method of claim 1, wherein the data further includes data representative of downtime for the equipment components, and wherein the parameter includes downtime.

14. A system for identifying training needs associated with a plurality biomedical equipment components in a medical institution, the system comprising:
- a central database configured to store data representative of the equipment components, the stored data including operation data and identification data identifying at least an equipment type;
- a data analysis module configured to arrange the operation data into groupings and to analyze the operation data based on the groupings, the groupings including an equipment type grouping; and
- a report generator configured to generate a report including an arrangement of the analyzed operation data based on the groupings, wherein a training need is identifiable based on the arrangement.

15. The system of claim 14, wherein the operation data includes breakdowns associated with the equipment components, and wherein the arrangement of the analyzed operation data comprises a presentation of the breakdowns associated with a particular equipment type.

16. The system of claim 14, wherein the operation data includes operator errors associated with the equipment components, and wherein the arrangement of the analyzed operation data comprises a presentation of the operator errors associated with a particular equipment type.

17. The system of claim 14, wherein the arrangement of the operation data includes a first presentation of the operation data for a particular medical facility and a second presentation of the operation data for a plurality of medical facilities.

18. The system of claim 17, wherein the medical facilities are at geographically diverse locations.

19. The system of claim 17, further comprising a user interface configured to provide access to the generated report.

20. The system of claim 19, wherein the report is generated at a location remote from the medical institution and is transmitted to the medical institution via a communication network.

21. The system of claim 20, wherein the communication network includes the Internet.

22. A method for identifying a training need associated with biomedical equipment in a medical institution, the method comprising:
- storing data associated with the equipment in a central database, the stored data including equipment operation data and equipment identification data;
- grouping the stored equipment operation data in accordance with the corresponding equipment identification data;
- analyzing the equipment operation data based on the grouping;
- generating a presentation of the analyzed equipment operation data in accordance with the grouping;
- identifying a training need associated with a particular piece of equipment based on the presentation; and
- outputting a report indicating the identified training need.

23. The method of claim 22, wherein the grouping comprises an equipment type grouping, an equipment manufacturer grouping, and an equipment location grouping.

24. The method of claim 23, wherein the equipment location grouping comprises locations of the pieces of equipment.

25. The method of claim 23, wherein the location grouping references a plurality of geographically diverse medical facilities.

26. The method of claim 22, wherein the operation data includes breakdowns and operator errors associated with the equipment.

27. A system for of identifying training needs for biomedical equipment in a medical facility, the system comprising:
- means for collecting identification and operation data associated with a plurality of biomedical equipment components;
- means for storing the collected data in a central database;
- means for analyzing the operation data to identify at least one operational parameter affected by operator activities with the equipment components; and
- means for identifying a training need based on the analyzed operational parameter.

* * * * *